(12) United States Patent
Besse

(10) Patent No.: US 6,531,151 B1
(45) Date of Patent: Mar. 11, 2003

(54) COMPOSITION CONTAINING HYDROXYPROPYLMETHYLCELLULOSE AND/OR ETHYLCELLULOSE AS DISINTEGRANTS AND PROCESS FOR PRODUCING IT

(75) Inventor: Jerome Besse, Listrac (FR)

(73) Assignee: Galenix Developpement (FR)

( * ) Notice: Subject to any disclaimer, the term of this patent is extended or adjusted under 35 U.S.C. 154(b) by 0 days.

(21) Appl. No.: 09/430,341

(22) Filed: Oct. 29, 1999

(51) Int. Cl.[7] .............................. A61K 9/20; A61K 9/22; A61K 9/24
(52) U.S. Cl. ...................... 424/464; 424/465; 424/466; 424/468; 424/472; 424/490
(58) Field of Search ................................ 424/464, 465, 424/472, 490, 468, 400, 466

(56) References Cited

U.S. PATENT DOCUMENTS

| | | |
|---|---|---|
| 4,795,327 A | 1/1989 | Gaylord et al. |
| 4,940,587 A | 7/1990 | Jenkins et al. |
| 4,992,277 A | 2/1991 | Sanagekar et al. |
| 5,403,593 A | 4/1995 | Royce |
| 5,681,583 A * | 10/1997 | Conte et al. ................ 424/472 |

FOREIGN PATENT DOCUMENTS

| | | |
|---|---|---|
| EP | 0223590 | 5/1987 |
| WO | 8700044 | 1/1987 |

* cited by examiner

*Primary Examiner*—Jose' G. Dees
*Assistant Examiner*—M. Haghighatian
(74) *Attorney, Agent, or Firm*—Bierman, Muserlian and Lucas

(57) ABSTRACT

Pharmaceutical composition comprising at least one active ingredient and hydroxypropylmethylcellulose, highly substituted hydroxypropylcellulose, and/or ethylcellulose as disintegrants, in quantities less than 15% by weight of the composition and in a form providing a disintegrant effect while avoiding the formation of a continuous matrix.

15 Claims, 6 Drawing Sheets

COMPOSITION CONTAINING HYDROXYPROPYLMETHYLCELLULOSE AND/OR ETHYLCELLULOSE AS DISINTEGRANTS AND PROCESS FOR PRODUCING IT

The present invention relates to a pharmaceutical composition containing hydroxypropylcellulose (HPC), hydroxypropylmethylcellulose (HPMC), and/or ethylcellulose (EC) as disintegrants.

It also relates to tablets composed of this composition.

A final object of the invention is a process for producing such tablets.

Various types of disintegrants are used in pharmaceutical compositions, at varying doses, depending on the effect sought for. The concentration of the disintegrant in the composition may be selected so as to achieve a more or less fast release of the active ingredient contained in the composition.

Cellulose derivatives are used as excipients: among these are the hydroxypropylcelluloses (HPC), the hydroxypropylmethylcelluloses (HPMC), and the ethylcelluloses (EC). There are two derivatives of the HPC, one highly substituted (H-HPC), and the other weakly substituted (L-HPC).

Thus, according to the monograph of the American Pharmacopoeia is (USP 23/NF 18), L-HPC has a substitution level of less than 10%. It is known for its qualities as a binder and a disintegrant.

H-HPC has a substitution level of the cellulose by hydroxypropoxy units of about 80%, as defined by the American Pharmacopoeia (USP 23/NF 18). This compound is known for its qualities as a binder.

L-HPC, although having satisfactory disintegrant properties, is a poor binding agent, whose unit cost is significantly higher than that of HPMC and H-HPC.

The problem at the root of the invention is to find agents whose general properties (toxicity, etc.) render them suitable for use in pharmaceutical compositions, and with binding and disintegrant properties presenting a compromise enabling them to form a discontinuous, or lacunary, matrix, making an effective disintegration possible, while retaining cohesion between the different constituents of the composition.

Such agents must in addition be active in small quantities, so that the active ingredients in the formulations remain the majority components.

The applicant has thus endeavored to find such an agent.

The applicant has unexpectedly demonstrated disintegrant properties of derivatives of H-HPC, HPMC and ethylcellulose (EC).

The present invention, in its most general form, thus concerns the use of hydroxypropylmethylcellulose (HPMC), highly substituted hydroxypropylcellulose (HPC), and/or ethylcellulose (EC) as disintegrants in pharmaceutical compositions.

For the purposes of the present invention, highly substituted hydroxypropylcellulose should be understood as any cellulose containing a minimum of 50%, preferably a minimum of 65%, and preferably a minimum of 75% of substitution by hydroxypropoxy groups.

Hydroxypropylmethylcellulose should be understood as any cellulose substituted by hydroxypropyl and methoxy groups, whatever the percentage of substitution. However, such a hydroxypropylmethylcellulose advantageously has a substitution level by hydroxypropoxy groups of between about 2 and 45%, and by methoxy groups of between about 10 and 40%.

The object of the invention is more precisely a pharmaceutical composition comprising at least one active ingredient and hydroxypropylmethylcellulose (HPMC), highly substituted hydroxypropylcellulose (HPC), and/or ethylcellulose (EC) as disintegrants, in quantities less than 15% by weight of the composition and in a form providing a disintegrant effect while avoiding the formation of a continuous matrix.

This absence, or quasi-absence, of a continuous matrix is demonstrated by the release profiles of the active ingredients. It may also be observed by cryofracture or by scanning electron microscopy.

Such a composition advantageously contains less than about 10% by weight of HPMC, highly substituted HPC and/or ethylcellulose, and preferably between about 1.5 and 7% by weight of HPMC, highly substituted HPC and/or ethylcellulose.

The use of hydroxypropylcellulose, hydroxypropylmethylcellulose or ethylcellulose as disintegrants allows the production of compositions, and in particular tablets, containing at least about 80%, preferably at least about 85% and even more preferably at least about 90% by weight of the active ingredients in the composition.

Such active ingredients may be any pharmacologically active molecules to be released into a liquid, either extracorporeal or intracorporeal.

Such an active ingredient is preferably paracetamol or diclofenac.

The compositions according to the present invention enable modulation of the kinetics of release of the active ingredient, as a function of the mode of incorporation and/or the concentration and/or the particle size of H-HPC, HPMC or EC.

The applicant has unexpectedly shown that the disintegrant power of H-HPC, HPMC and EC is inversely proportional to their particle size. The compositions according to the present invention advantageously contain H-HPC, HPMC or EC in micronized form. These cellulose derivatives are preferably present in the form of powders with an average diameter of less than about 50 $\mu$m. Such a diameter allows the total quantity of these cellulose derivatives to be reduced to 2.5%.

The composition may in addition contain at least one binding agent, so as to maintain the bond between the excipients constituting the composition. The binding agent may in particular be polyvinylpyrrolidone (PVP) or methyl polymethacrylate.

It may also be HPMC, H-HPC or EC in a form enabling an binding effect to be obtained, in other words added during the manufacture of the composition in solution form, and not micronized.

Although the present invention preferentially relates to tablets, the composition according to the present invention may also be in the form of powder, granules, or any other pharmaceutical form, selected as a function of the active ingredient which it is desired to administer, and of the mode of administration.

A person skilled in the art could determine, for each active ingredient, the appropriate quantities of highly substituted hydroxypropylcellulose, hydroxypropylmethylcellulose and/or ethylcellulose, in particular by using the dissolution tests described in the European Pharmacopoeia (1997, Pharmotechnical Methods, p. 127 to 130). These tests are performed by placing a granule or a tablet containing the active ingredient in a blade, bucket or continuous flow apparatus and observing the kinetics of release of the active ingredient. The skilled person could thus simply and reliably determine the quantities of highly substituted hydroxypropylcellulose, hydroxypropylmethylcellulose, and/or ethylcellulose and adjust the release (immediate or sustained) depending on the therapeutical needs.

These granules or tablets preferably comprise at least two phases.

According to a first embodiment, the active ingredients and H-HPC, HPMC and/or EC are comprised in the same phase.

They may however, according to a second embodiment, be comprised in two phases.

According to a third embodiment, the active ingredients and H-HPC, HPMC and/or EC are present in different phases.

According to a particularly advantageous embodiment of the present invention, the granules or tablets comprise two cores, the first or inner core, composed of a composition according to the present invention and comprising a certain quantity of one or more active ingredients.

The outer core comprises at least an effective quantity of one or more active ingredients and at least one compound with a strong disintegrant effect, but is composed of a composition different from that which is the object of the present invention. Such a composition allows immediate release of the active ingredients which it contains.

Such an embodiment of the present invention is particularly advantageous since it allows immediate release of a high dose of the active ingredient by dissolution of the outer core, and then release in delayed fashion of the active ingredient(s) contained in the inner core.

The inner core may itself be composed of two phases, inner and outer, of a composition according to the present invention.

Such an embodiment of the present invention is advantageously used with paracetamol as active ingredient.

The granules or tablets according to the present invention may be obtained by techniques known to a person skilled in the art, by granulation by dry or wet methods, or by direct compression for the tablets.

The granules may in particular be packaged into capsules, or into sachets.

According to a first method, the active ingredient(s) is (are) mixed in the inner phase with a binding agent in aqueous or organic solution, for example polyvinylpyrrolidone derivatives or cellulose derivatives such as HPMC or ethylcellulose. The HPMC, H-HPC or EC are added to the outer phase with a lubricant, for example magnesium stearate.

According to a second method, the active ingredient is mixed in the inner phase with HPMC or H-HPC or EC and a binding agent, for example PVP. These are mixed until a homogenous mixture is obtained. A binding solution is added and the mixture is then granulated. To the inner granule is added a lubricant as outer phase, for example magnesium stearate. The resulting composition then passes to the compression stage.

According to a third method, the active ingredient is mixed with H-HPC, HPMC or EC and an excipient in current use for direct compression such as lactose, starch or microcrystalline cellulose. A lubricant is added and the mixture is compressed.

In general, a person skilled in the art could refer to the general manual "Abrégé de pharmacie galénique", Le HIR, Editions Masson, for the application of the present invention, and particularly for the preparation of compositions.

The present invention is illustrated without in any way being limited by the following examples.

It is also illustrated by FIGS. 1 to 8.

EXAMPLE 1

Figure 1:
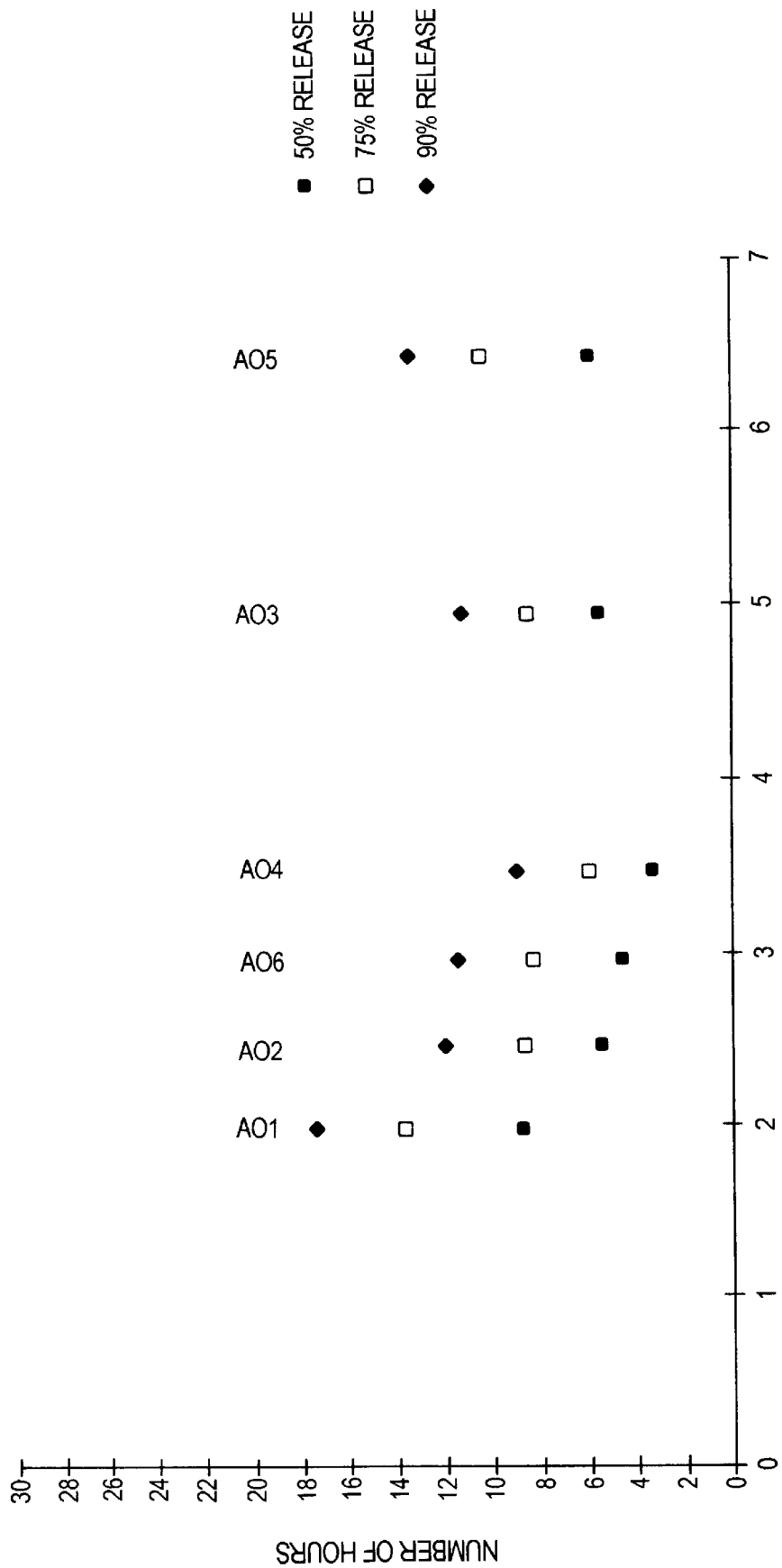
FIG. 1 shows the release of 50%, 75% and 90% of diclofenac in various tablet formulations containing hydroxypropylcellulose (H-HPC) in their outer phase, as a function of time.

Manufacture of Two-Phase Diclofenac Tablets Containing Highly Substituted Hydroxypropycellulose in the Outer Phase Granulation 1. The different excipients of the inner phase are introduced into a TURBULA mixer or equivalent apparatus and mixed for 15 minutes.
2. The mixture is transferred into a shaker operating at low speed and a binder (polyvinylpyrrolidone K90, 5% in water) is added.
3. The granules are dried in a drying chamber until a humidity level of 2 to 4% is reached. Such a drying typically takes 12 hours at 40° C.
4. The dried granules are passed into an ERWEKA AR 400 granulator fitted with a 0.8 mm mesh.

Addition of the outer phase

1. The granules are transferred into a TURBULA type mixer and hydroxypropylcellulose (H-HPC) is added. The whole is mixed for 15 minutes.
2. A part of the mixture obtained is mixed with magnesium stearate or other lubricant.
3. The mixture thus obtained is added to the remainder of the mixture from step 1, and the whole is mixed for 15 minutes in the same mixer.

This process gives the following tablets:

| Theoretical weight per tablet: 771.14 mg | | |
|---|---|---|
| A01 | % | mg/tablet |
| Inner phase | | |
| DICLOFENAC | 97.27 | 750 |
| Colloidal silica AEROSIL 200 | 0.2 | 1.60 |
| Polyvinylpyrrolidone K90 (5% in water) | 1.53 | 11.83 solid |
| Outer phase | | |
| Hydroxypropylcellulose Klucel HXF | 0 | 0 |
| Magnesium stearate | 1 | 7.71 |

| Theoretical weight per tablet: 786.95 mg | | |
|---|---|---|
| A02 | % | mg/tablet |
| Inner phase | | |
| DICLOFENAC | 95.3 | 750 |
| Colloidal silica AEROSIL 200 | 0.2 | 1.59 |

-continued

Theoretical weight per tablet: 786.95 mg

| A02 | % | mg/tablet |
|---|---|---|
| Polyvinylpyrrolidone K90 (5% in water) | 1.51 | 11.86 solid |
| Outer phase | | |
| Hydroxypropylcellulose Klucel HXF | 1.99 | 15.62 |
| Magnesium stearate | 1 | 7.88 |

Theoretical weight per tablet: 811.75 mg

| A03 | % | mg/tablet |
|---|---|---|
| Inner phase | | |
| DICLOFENAC | 92.39 | 750 |
| Colloidal silica AEROSIL 200 | 0.2 | 1.59 |
| Polyvinylpyrrolidone K90 (5% in water) | 1.46 | 11.86 solid |
| Outer phase | | |
| Hydroxypropylcellulose Klucel HXF | 4.95 | 40.20 |
| Magnesium stearate | 1 | 8.10 |

Theoretical weight per tablet: 799.17 mg

| A04 | % | mg/tablet |
|---|---|---|
| Inner phase | | |
| DICLOFENAC | 93.85 | 750 |
| Colloidal silica AEROSIL 200 | 0.2 | 1.60 |
| Polyvinylpyrrolidone K90 (5% in water) | 1.48 | 11.83 solid |
| Outer phase | | |
| Hydroxypropylcellulose Klucel HXF | 3.47 | 27.71 |
| Magnesium stearate | 1 | 8.02 |

Theoretical weight per tablet: 790.92 mg

| A05 | % | mg/tablet |
|---|---|---|
| Inner phase | | |
| DICLOFENAC | 90.94 | 750 |
| Colloidal silica AEROSIL 200 | 0.19 | 1.60 |
| Polyvinylpyrrolidone K90 (5% in water) | 1.43 | 11.83 solid |
| Outer phase | | |
| Hydroxypropylcellulose Klucel HXF | 6.43 | 53.06 |
| Magnesium stearate | 1 | 8.24 |

Theoretical weight per tablet: 794.99 mg

| A06 | % | mg/tablet |
|---|---|---|
| Inner phase | | |
| DICLOFENAC | 94.34 | 750 |
| Colloidal silica AEROSIL 200 | 0.2 | 1.56 |
| Polyvinylpyrrolidone K90 (5% in water) | 1.49 | 11.85 solid |
| Outer phase | | |
| Hydroxypropylcellulose Klucel HXF | 2.97 | 23.62 |
| Magnesium stearate | 1 | 7.94 |

Theoretical weight per tablet: 790.92 mg

| A07 | % | mg/tablet |
|---|---|---|
| Inner phase | | |
| DICLOFENAC | 94.83 | 750 |
| Colloidal silica AEROSIL 200 | 0.2 | 1.56 |
| Polyvinylpyrrolidone K90 (5% in water) | 1.50 | 11.85 solid |
| Outer phase | | |
| Hydroxypropylcellulose Klucel HXF | 2.47 | 19.54 |
| Magnesium stearate | 1 | 7.94 |

The release times for 50%, 75% or 90% of diclofenac were measured.

Figure 2:
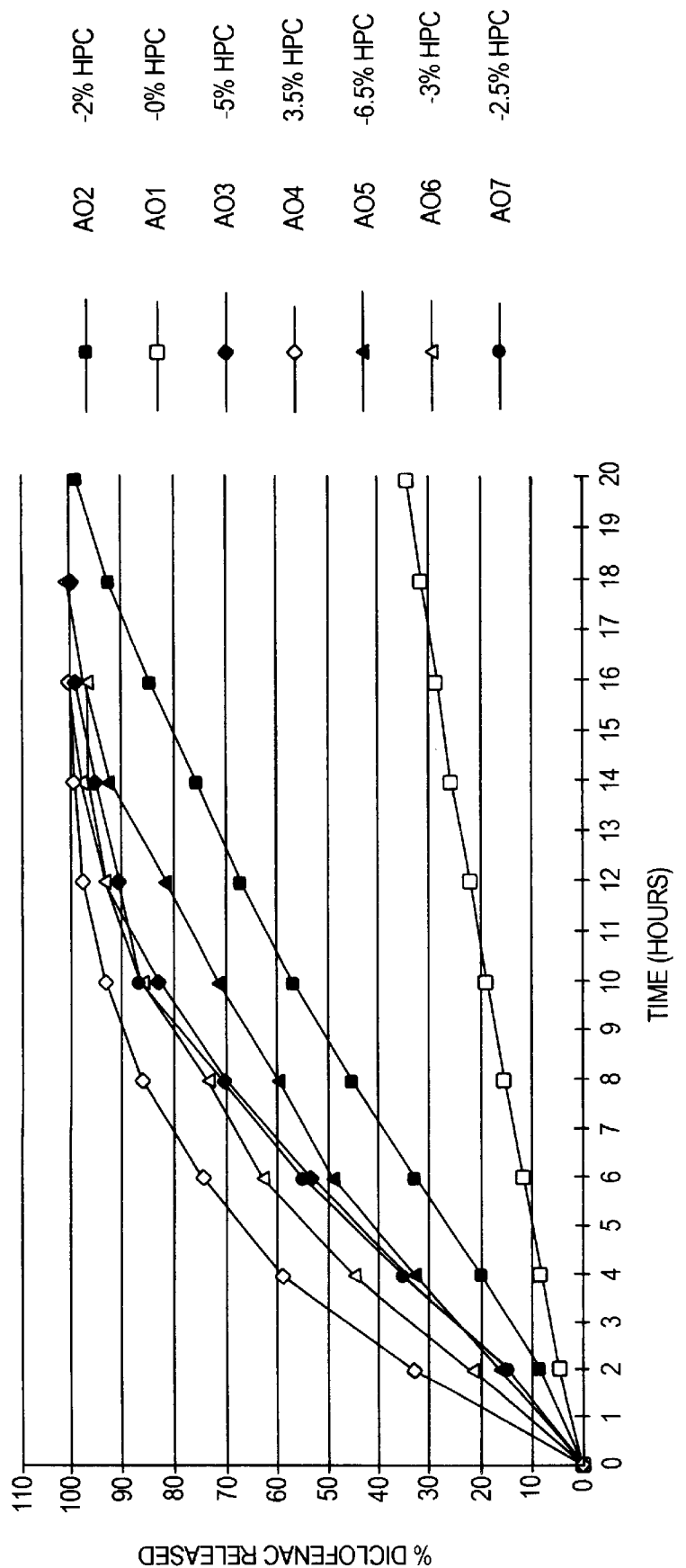
FIG. 2 shows the kinetics of release of the compositions of FIG. 1.

The results of these measurements are summarized in FIG. 1. The kinetics of release of diclofenac as a function of time are illustrated in more detail by FIG. 2.

These results clearly show that the formulations according to the present invention lead to an immediate release of diclofenac, with an optimal release time for composition A04, which has a hydroxypropylcellulose percentage of 3.5%.

EXAMPLE 2

Manufacture of Two-Phase Paracetamol Tablets Containing Hydroxypropylmethylcellulose in the Outer Phase.

1) Inner Phase

Introduce the paracetamol into a planetary type mixer or equivalent.

Add the PVP binder solution (KOLLIDON 90F).

Dry the granules until the required residual humidity level is reached, either with an oven, or with a fluidized air bed dryer.

Proceed to the granulation step.

2) Final Mixture

Add the excipients of the outer phase (HPMC, METO-LOSE 90 SH 4000 SR) and magnesium stearate to a planetary type mixer.

Proceed to the compression step on a suitable machine (alternating or rotary).

The two tablets whose compositions are given below, named 071.03 and 071.04, were prepared and compressed with four different compression forces: 60 N, 80 N, 100 N and 120N.

| Theoretical weight per tablet: 709.22 | | | |
|---|---|---|---|
| 071.03 | mg | % | batch (g) |
| Inner phase | | | |
| PARACETAMOL | 650 | 91.65 | 139.18 |
| Kollidon 90F - Povidone 90 | 20.21 | 2.85 | 4.33 |
| Outer phase | | | |
| HPMC (Metolose 90 SH 4000 SR) | 35.46 | 5 | 7.59 |
| Magnesium stearate | 3.55 | 0.5 | 0.76 |

| Theoretical weight per tablet: 707.06 mg | | | |
|---|---|---|---|
| 071.04 | mg | % | batch (g) |
| Inner phase | | | |
| PARACETAMOL | 650 | 91.93 | 148.44 |
| Kollidon 90F - Povidone 90 | 18.17 | 2.57 | 4.15 |
| Outer phase | | | |
| HPMC (Metolose 90 SH 4000 SR) | 35.35 | 5 | 8.07 |
| Magnesium stearate | 3.54 | 0.5 | 0.81 |

Figure 3:
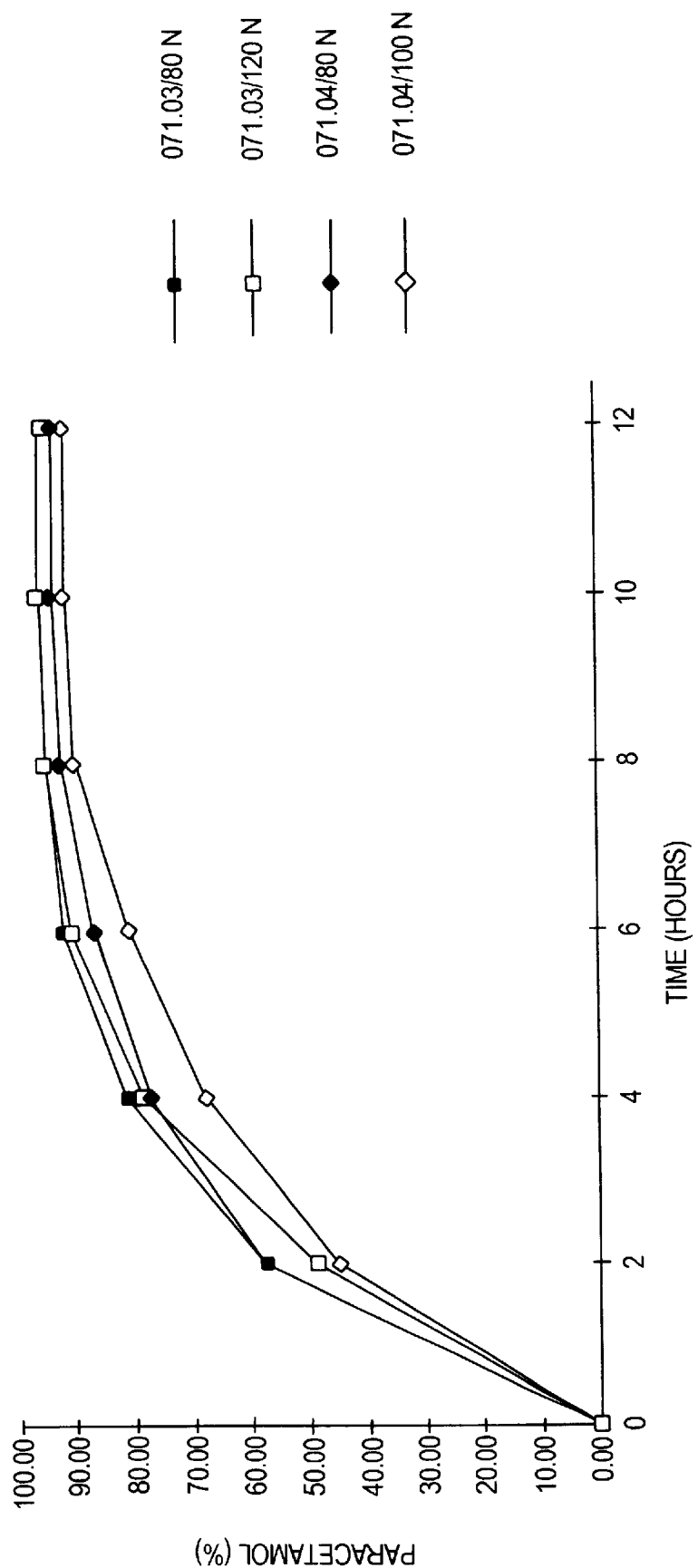
FIG. 3 shows the kinetics of release of paracetamol in tablet formulations containing hydroxypropylcellulose in their outer phase.

The release of paracetamol was measured for four of these preparations: 071.03/80 N, 071.03/120 N, 071.04/80 N, 071.04/100 N. The results of these release tests are shown in FIG. 3.

EXAMPLE 3
Preparation of Two-Phase Paracetamol Tablets Containing Hydroxypropylmethylcellulose in the Inner Phase 1) Inner Phase
   Introduce the paracetamol, the HPMC (METOLOSE 90 SH 4000 SR) and the PVP as powder into a planetary type mixer or equivalent.
   Mix until a homogeneous mixture is obtained.
   Add the binder solution of 10% PVP.
   Dry the granules until the required residual humidity level is reached (about 3%), either with an oven, or with a fluidized air bed dryer.
   Proceed to the granulation step using a 0.8 mm mesh.
2) Final Mixture
   Add the excipients of the outer phase, i.e. magnesium stearate, to a planetary type mixer.
   Proceed to the compression step on a suitable machine (alternating or rotary).
   The following tablets were obtained.

| | PLP5 | PLP6 | PLP7 | PLP8 |
|---|---|---|---|---|
| Inner phase | | | | |
| Paracetamol | 90% | 90% | 94.5% | 90% |
| HPMC 90 SH 4000 | 4.5% | | | 2.25% |
| PVP K90 (powder) | 2.75% | 2.75% | 2.75% | 2.75% |
| PVP K90 (10% solution) | 2.25% | 2.25% | 2.25% | 2.25% |
| Outer phase | | | | |
| HPMC 90 SH 4000 SR | | 4.5% | | 2.25% |
| Magnesium stearate | 0.5% | 0.5% | 0.5% | 0.5% |

Figure 4:
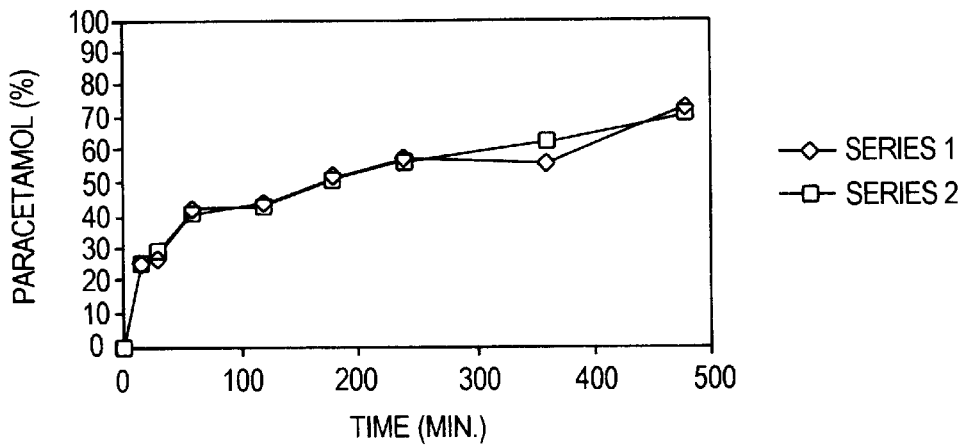
FIGS. 4 to 6 illustrate the release of paracetamol by granules containing HPMC in their inner phase (FIG. 4), their outer phase (FIG. 5), or not containing HPMC (FIG. 6).
Figure 5:
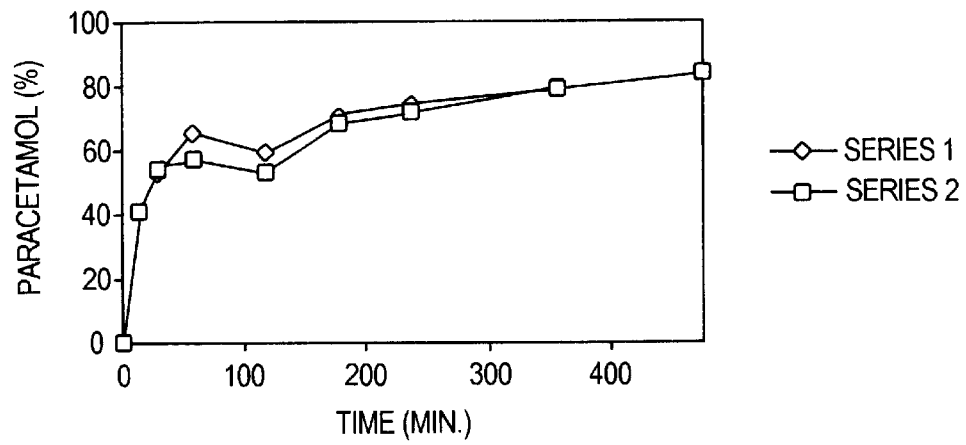
Figure 6:
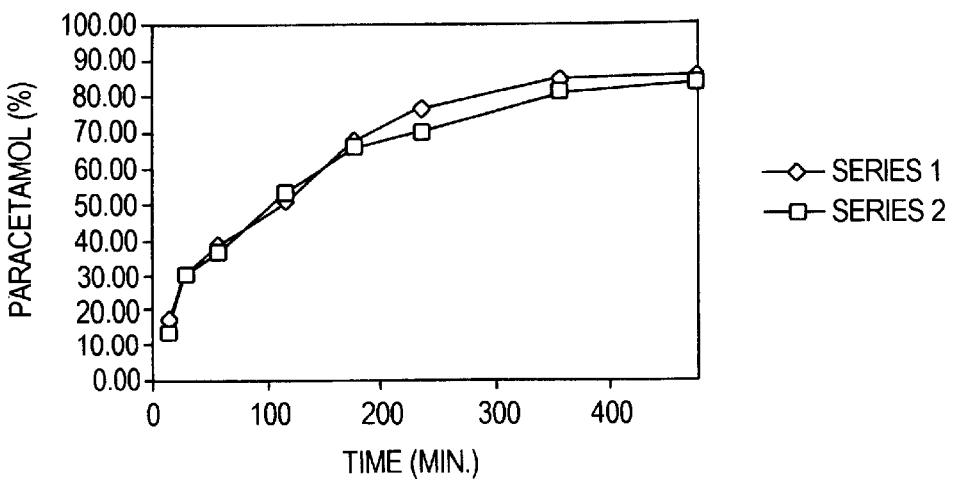

The release of paracetamol was tested for preparations PLP5, PLP6 and PLP7. The kinetics of release are shown on FIGS. 4, 5 and 6, respectively.

EXAMPLE 4
Preparation of Double-Core Paracetamol Tablets

The double-core tablets were composed of an inner core (GAL-135-04) and an outer core surrounding the inner core.

The inner core was prepared as described in example 3 for the two-phase tablet.

The respective quantities of the different components were significantly changed and are as follows:

| Composition of the inner core gal 135.04 (sustained) | | |
|---|---|---|
| | Percentage composition | Quantity per unit (mg) |
| Inner phase | | |
| Paracetamol | 96.0 | 400 |
| Hydroxypropylmethyl-cellulose (metolose 90SH 4000 SR) | 2.0 | 8.34 |
| Povidone K90 (powder) | 1.5% | 6.25 |
| Outer phase | | |
| Magnesium stearate | 0.5% | 2.08 |
| TOTAL | 100 | 416.67mg |

The inner core thus prepared was placed in the compression chamber of a compressor previous filled with half the composition constituting the outer core.

The second half of the composition constituting the outer core was then added, and the whole was compressed so as to produce a double-core tablet with the following composition:

| Composition of the double-core tablets GAL 135.05 | | |
|---|---|---|
| | Percentage composition | Quantity per unit (mg) |
| Outer phase (immediate) | | |
| Paracetamol | 36.56 | 500 |
| PVP K30 | 1.13 | 15.46 |
| L HPC 21 | 1.17 | 16.02 |
| Magnesium stearate | 0.20 | 2.67 |
| Inner phase (sustained) | | |
| GAL 135.04 | 60.94 | 416.67 |
| TOTAL | 100 | 950.82 |

The GAL 135.05 tablets thus obtained were composed of a two-phase inner core (GAL 135.04) and a single-phase outer core.

The dissolution kinetics of these tablets were tested in vitro in accordance with the recommendations of the Pharmacopoeia cited above.

Figure 7:
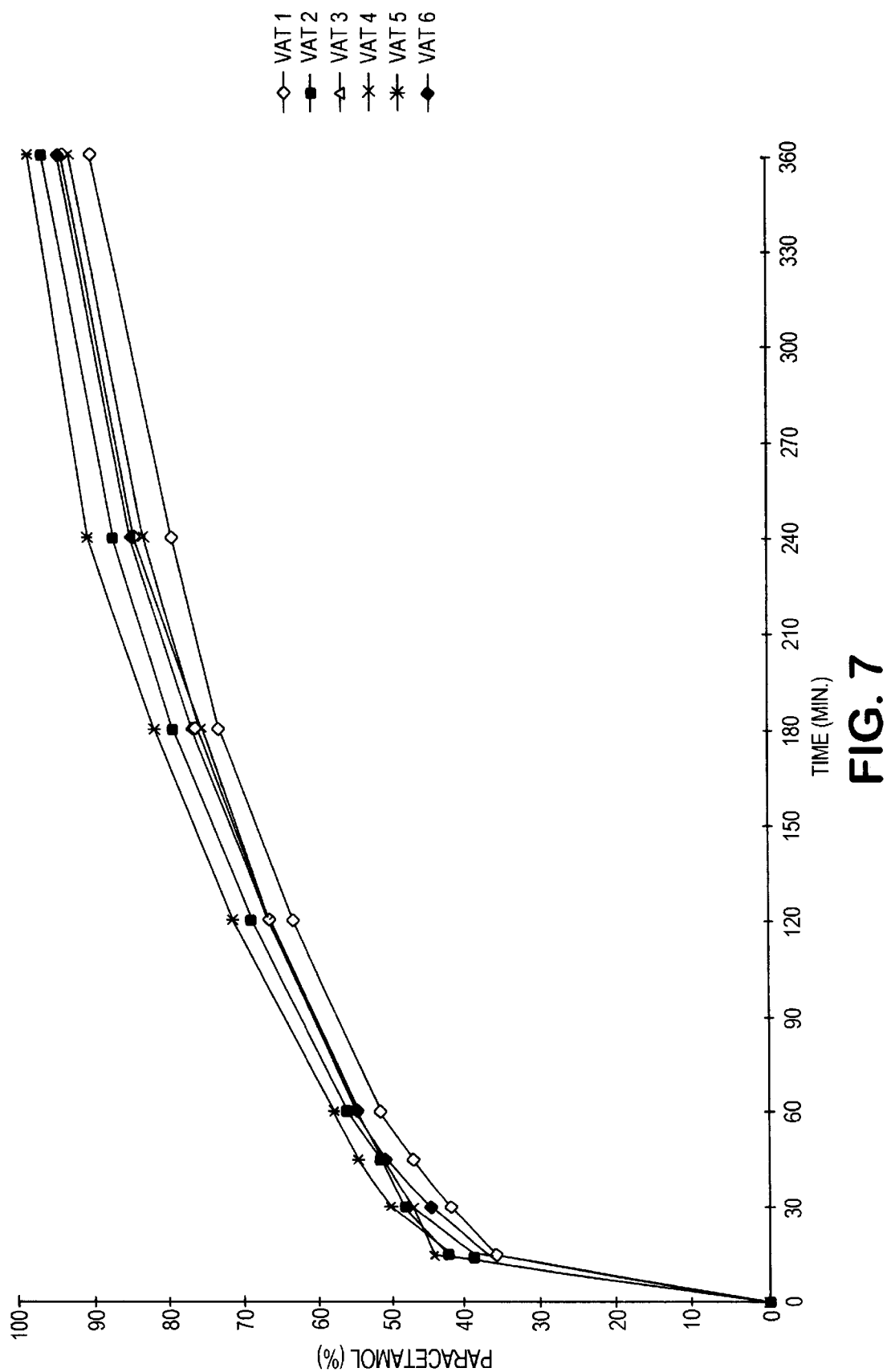
FIG. 7 shows the release of paracetamol from 6 double-core tablets.
Figure 8:
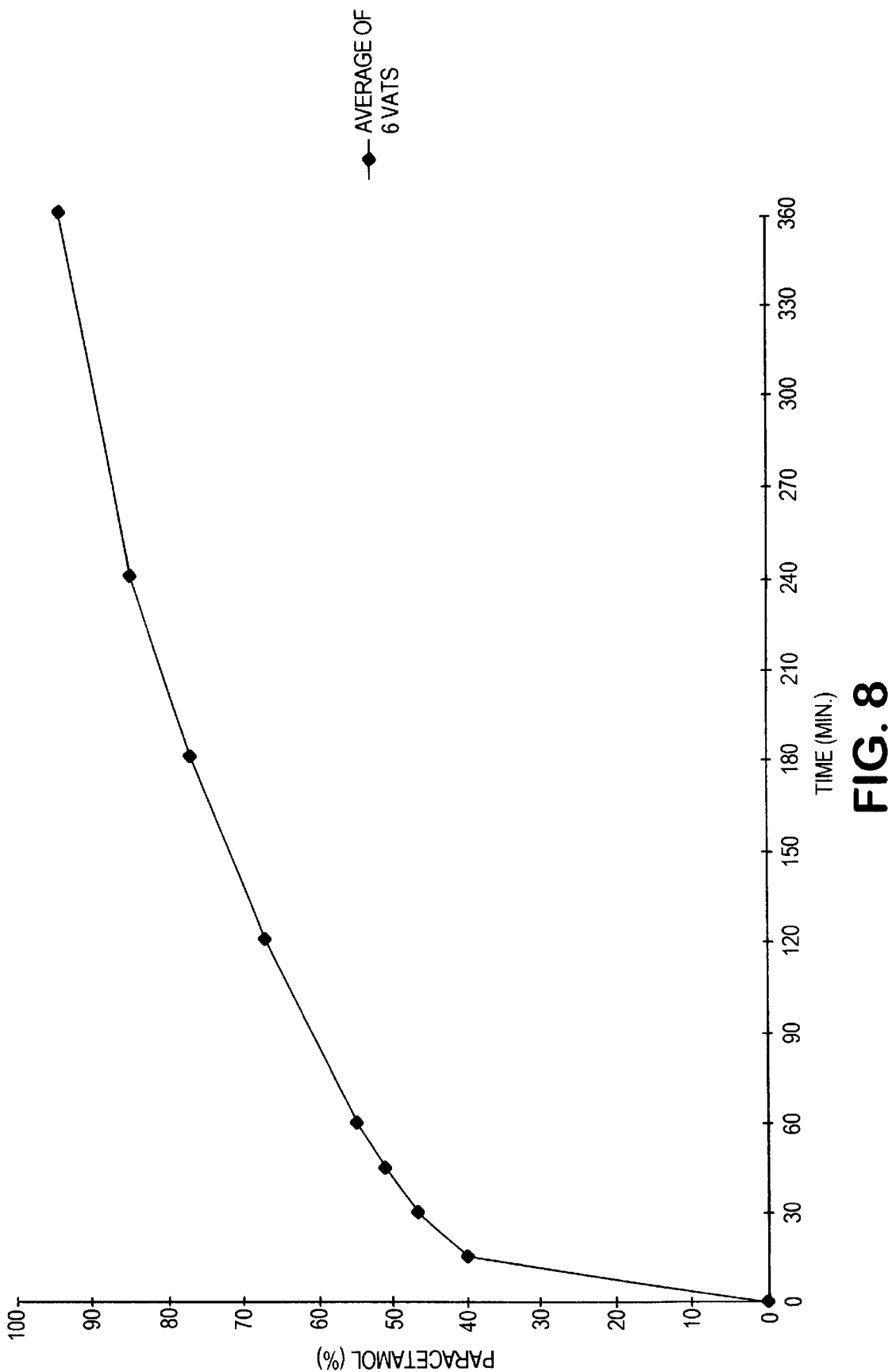
FIG. 8 is an average of the results obtained with these 6 tablets.

The results of these tests are shown in the table below and in the graphs in FIGS. 7 and 8. The graph in FIG. 8 is the average of the six graphs of FIG. 7.

It seems that about 40% of the paracetamol dose is released in the first 15 minutes and that delayed release then occurs up to 6 hours after the beginning of the study.

These tablets thus give an immediate release of part of the paracetamol contained in the outer core, while the paracetamol contained in the inner core is released more slowly.

TABLE

In vitro dissolution of GAL 131.05

Determination: Paracetamol
Method: HPLC
Medium: Buffer pH = 5.8
Stirrer rotation: 50 r.p.m.

| Time (minutes) | Vat 1 | Vat 2 | Vat 3 | Vat 4 | Vat 5 | Vat 6 | Average | CV (%) |
|---|---|---|---|---|---|---|---|---|
| | | | | % Active | | | | |
| 0 | 0.00 | 0.00 | 0.00 | 0.00 | 0.00 | 0.00 | 0.00 | 0 |
| 15 | 35.74 | 42.11 | 38.60 | 43.95 | 41.84 | 36.98 | 39.87 | 8.14 |
| 30 | 41.77 | 48.19 | 46.87 | 47.26 | 50.08 | 44.44 | 46.44 | 6.31 |
| 45 | 46.99 | 51.53 | 51.19 | 51.12 | 54.59 | 50.93 | 51.06 | 4.74 |
| 80 | 51.58 | 56.06 | 55.08 | 54.80 | 57.89 | 54.64 | 55.01 | 3.75 |
| 120 | 63.35 | 68.81 | 66.78 | 66.34 | 71.42 | 66.72 | 67.23 | 4.01 |
| 180 | 73.01 | 79.31 | 75.34 | 75.89 | 81.73 | 76.54 | 76.99 | 4.01 |
| 240 | 79.39 | 87.11 | 84.34 | 83.06 | 90.66 | 84.81 | 84.90 | 4.47 |
| 320 | 90.14 | 96.72 | 94.04 | 93.00 | 98.54 | 94.42 | 94.48 | 3.10 |
| Theor. wt. (mg) | 683.74 | 683.74 | 683.74 | 683.74 | 683.74 | 683.74 | | |
| Expt. wt. (mg) | 706.9 | 711 | 706 | 708.3 | 686.7 | 703.8 | | |

What is claimed is:

1. A pharmaceutical composition in the form of a powder, granule or tablet comprising at least one active ingredient and at least one member selected from the group consisting of hydroxypropylmethylcellulose, hydroxypropylcellulose containing a minimum of 50% of substitution by hydroxypropoxy groups, and ethylcellulose as disintegrants, in an amount of less than 15% by weight of the composition and in a form providing a disintegrant effect while avoiding the formation of a continuous matrix and wherein the composition comprises at least about 80% of active ingredients by weight of the composition.

2. The composition of claim 1 wherein it contains less than about 10% by weight of the disintegrant.

3. The composition of claim 1 wherein it contains between about 1.5 and 7% by weight of disintegrant.

4. The composition of claim 1 wherein the hydroxypropylmethylcellulose advantageously has a substitution level by hydroxypropoxy groups of between about 2 and 45% and by methoxy groups of between 10 and 40%.

5. The composition of claim 1 wherein the disintegrant is in micronized form.

6. The composition of claim 1 wherein the disintegrant is in the form of powders with an average diameter of less than about 50 μm.

7. The composition of claim 1 wherein it contains at least 85% by weight of the active ingredient.

8. The composition of claim 1 wherein it additionally contains at least one binding agent.

9. A tablet or granule of claim 1.

10. A tablet or granule of claim 11 wherein it comprises at least two layers.

11. A tablet or granule of claim 9 wherein the active ingredient and the disintegrant are comprised in the same layer.

12. A tablet or granule of claim 9 wherein the active ingredient and the disintegrant are comprised in two layers.

13. A tablet or granule of claim 9 wherein the active ingredient or ingredients and the disintegrant are comprised in different layers.

14. A tablet or granule of claim 9 wherein it is composed of an inner core and an outer core, the inner core comprising a composition of claim 1, and the outer core comprising at least one compound with a disintegrant effect and an effective amount of the active ingredient contained in the inner core.

15. A pharmaceutical composition in the form of a powder, granule or tablet comprising at least one active ingredient of paracetamol or diclofenac and at least one member selected from the group consisting of hydroxypropylmethylcellulose, hydroxypropylcellulose containing a minimum of 50% of substitution by hydroxypropoxy groups, and ethylcellulose as disintegrants, in an amount of less than 15% by weight of the composition and in a form providing a disintegrant effect while avoiding the formation of a continuous matrix and wherein the composition comprises at least 80% of active ingredients by weight of the composition.

* * * * *